March 18, 1958 A. L. STROH Plant Pat. 1,693
BEGONIA PLANT
Filed March 19, 1957
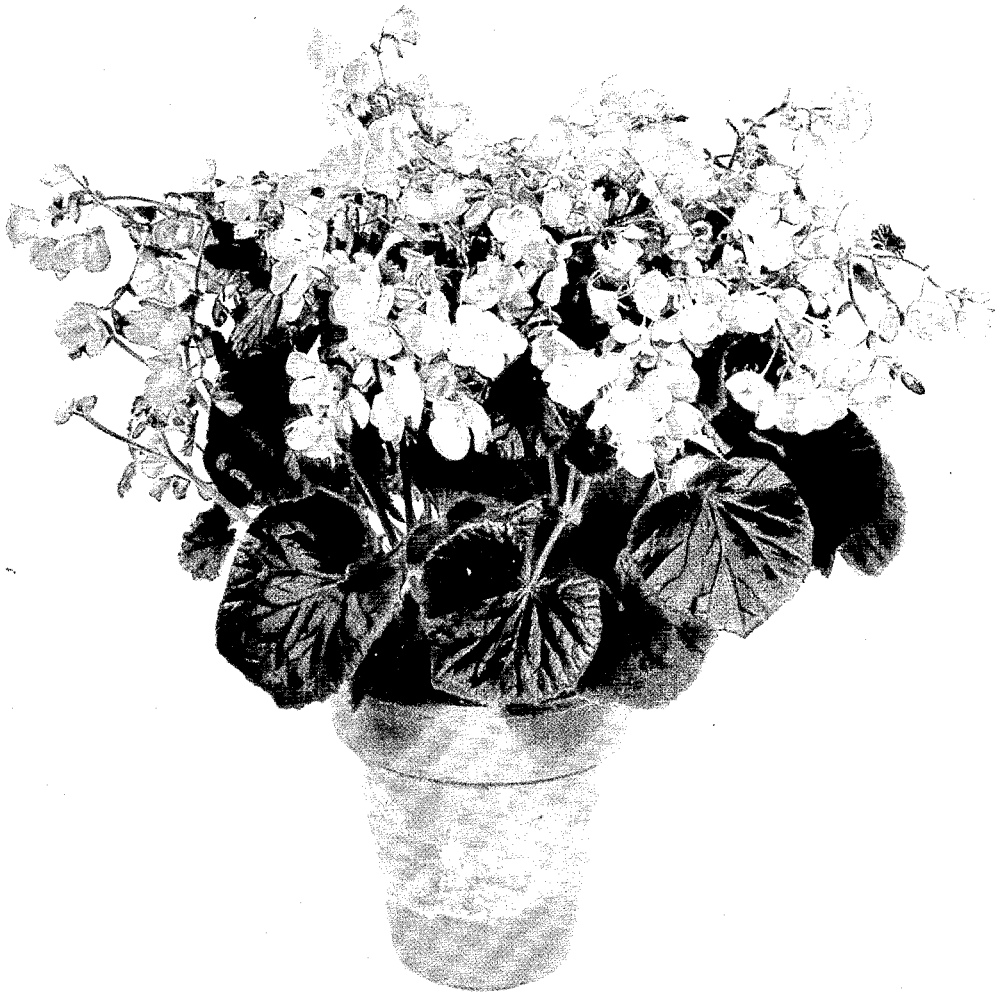
INVENTOR
Albert L. Stroh,
BY Raymon E. Rousseau
ATTORNEY.

United States Patent Office

Plant Pat. 1,693
Patented Mar. 18, 1958

1,693

BEGONIA PLANT

Albert L. Stroh, Batavia, N. Y.

Application March 19, 1957, Serial No. 647,174

1 Claim. (Cl. 47—60)

The present invention relates to a new and distinct variety of a winter flowering type of begonia which is a sport mutation of an unpatented variety known as Lady Mac.

This new variety was discovered by me in 1953 in a glass house under my supervision and control at Batavia, New York; has been carefully watched, cultivated and nurtured by me and has been asexually reproduced by me and under my supervision in the above identified glass house.

The asexual reproduction of my new sport has been by removing leaves therefrom, rooting and growing such leaves into stock plants and removing, rooting and growing the leaves of said plants into other plants. Each successive generation of plants has remained true to the type and the herein described characteristics of the first plant. The propagation of some two thousand plants over a period of over three years shows that the qualities and characteristics of my new plant are permanently fixed.

The most prominent characteristics, which readily distinguish my new plant from its parent, Lady Mac, are the greater substance of its main stems, branches, leaf stems and leaves, the much darker green coloring and the glossy leathery appearance of its leaves, its habit of forming and issuing more main stems from its crown and its habit of branching more freely to provide a bushier plant.

Other characteristics of my plant, which are improvements over Lady Mac, are its somewhat greater profusion of slightly larger pink blooms which have a discernably deeper shade of pink coloring, which hold their color better and longer and which in sunlight become brighter instead of fading.

The accompanying illustration shows the form of a typical specimen of my new variety of begonia plant, the coloring of which is shown as nearly true as is possible in this type of illustration.

The following is a detailed description of my new variety of begonia plant in which the references to its colors are based on Ridgway's Color Standards and Nomenclature:

*The plant*

Growth: A crown is formed at the end of the rooted cutting and the roots form from this crown. A number of sturdy main stems grow directly from the crown and these stems branch freely to provide a plant which is bushier than its parent.

Blooming: Blooms abundantly from about the middle of October to about the middle of January.

Foliage: Abundant; overlapping.

Leaves (mature): Front—Dark Dull Yellow-Green (1) XXXII edged with Indian Red XXVII. Back—Malachite Green XXXII edged with Hydrangea Red XXVII.

Leaves (immature): Front—Deep Dull Yellow-Green XXXII.

*The flower*

Buds: Rose Red Pl. XII.

Flower: Rose color Pl. XII blended with Spinel Red Pl. XII.

Stems (mature): Winter Green XVII.

Stems on flowers: Light Paris Green XVII and Pinkish Vinaceous XXVII.

Having thus disclosed my discovery, I claim:

A new and distinct variety of winter blooming begonia, of the Lady Mac type, characterized particularly by its habit of forming and issuing a number of main stems directly from its crown, its habit of branching more freely, the greater substance and sturdiness of its main stems, branches, leaf stems and leaves, the leathery appearance of its darker green glossy leaves, and its greater profusion of pink flowers which are larger, deeper colored and hold their color better and longer than its parent, Lady Mac.

No references cited.